(12) United States Patent
Guo et al.

(10) Patent No.: US 11,434,187 B2
(45) Date of Patent: Sep. 6, 2022

(54) SYSTEM OF CONCENTRATING AND SEPARATING WASTE SOLVENT LIQUID

(71) Applicant: ECOVE Waste Management Corporation, Taichung (TW)

(72) Inventors: Yu-Ling Guo, Taichung (TW); Ming-Chih Lin, Taichung (TW); Hsin-Hui Yen, Taichung (TW); Cheng-Tse Hsu, Taichung (TW); Che-Yu Chen, Taichung (TW)

(73) Assignee: ECOVE WASTE MANAGEMENT CORPORATION, Taichung (TW)

( * ) Notice: Subject to any disclaimer, the term of this patent is extended or adjusted under 35 U.S.C. 154(b) by 0 days.

(21) Appl. No.: 17/141,817

(22) Filed: Jan. 5, 2021

(65) Prior Publication Data

US 2022/0213013 A1 Jul. 7, 2022

(51) Int. Cl.
| | |
|---|---|
| *C07C 29/82* | (2006.01) |
| *B01D 3/36* | (2006.01) |
| *B01D 5/00* | (2006.01) |
| *B01D 3/14* | (2006.01) |
| *B01D 3/40* | (2006.01) |
| *B01D 11/04* | (2006.01) |

(52) U.S. Cl.
CPC ............ *C07C 29/82* (2013.01); *B01D 3/145* (2013.01); *B01D 3/36* (2013.01); *B01D 3/40* (2013.01); *B01D 5/006* (2013.01); *B01D 5/009* (2013.01); *B01D 11/0415* (2013.01)

(58) Field of Classification Search
CPC ........ B01D 5/006; B01D 5/009; B01D 3/145; B01D 3/36; B01D 3/40; B01D 11/0415; C07C 29/82
See application file for complete search history.

(56) References Cited

U.S. PATENT DOCUMENTS

| | | | | |
|---|---|---|---|---|
| 4,978,430 A | * | 12/1990 | Nakagawa | B01D 53/22 159/DIG. 27 |
| 5,035,776 A | * | 7/1991 | Knapp | C07C 29/84 203/19 |

(Continued)

FOREIGN PATENT DOCUMENTS

TW M583450 U * 9/2019 ................ C02F 1/38

*Primary Examiner* — Jonathan Miller
(74) *Attorney, Agent, or Firm* — Muncy, Geissler, Olds & Lowe, P.C.

(57) ABSTRACT

A system of concentrating and separating waste solvent liquid includes a distillation tower, an extracting distillation unit, an extract agent recovery unit, and a vapor permeation film unit. The scheme of centrifugal distillation is specifically employed to collocate with vapor permeation to effectively concentrate the content of isopropanol in the waste solvent liquid to generate a final produce with ultra high concentration of isopropanol, and constantly recovers the extract agent. The system is able to be quickly settled to a steady state of operation with low power consumption because the extracting distillation unit has smaller size. Since no liquid is left in the extract agent recovery unit, operation risk is greatly reduced. In addition, the input feed is almost processed, overall efficiency is thus improved. The vapor permeation film unit further removes considerably little content of water from the organic solvent to increase the content of isopropanol up to 99.9% or more.

13 Claims, 5 Drawing Sheets

(56) References Cited

U.S. PATENT DOCUMENTS

| | | | | |
|---|---|---|---|---|
| 5,105,029 | A * | 4/1992 | Ninomiya | C07C 29/76 |
| | | | | 568/747 |
| 7,594,981 | B2 * | 9/2009 | Ikeda | B01D 3/14 |
| | | | | 203/18 |
| 8,114,255 | B2 * | 2/2012 | Vane | C12P 7/06 |
| | | | | 203/12 |
| 8,128,787 | B2 * | 3/2012 | Wynn | B01D 61/362 |
| | | | | 203/12 |
| 8,263,815 | B2 * | 9/2012 | Huang | B01D 3/14 |
| | | | | 568/917 |
| 9,000,235 | B2 * | 4/2015 | Lee | C07C 29/147 |
| | | | | 568/885 |
| 9,138,678 | B2 * | 9/2015 | Huang | B01D 71/44 |
| 9,221,729 | B1 * | 12/2015 | Lee | C10G 21/27 |
| 2009/0255853 | A1 * | 10/2009 | Lee | C10G 21/06 |
| | | | | 208/312 |
| 2012/0010445 | A1 * | 1/2012 | Johnston | C07C 29/149 |
| | | | | 568/885 |
| 2021/0053893 | A1 * | 2/2021 | Tian | B01D 3/40 |

\* cited by examiner

SYSTEM OF CONCENTRATING AND SEPARATING WASTE SOLVENT LIQUID

BACKGROUND OF THE INVENTION

1. Field of the Invention

The present invention generally relates to a system of concentrating and separating waste solvent liquid, and more specifically to a system of concentrating and separating waste solvent liquid employing a distillation tower in collocation with an extracting distillation unit, an extract agent recovery unit, and a vapor permeation film unit connected in series for processing a waste solvent mixture with a lower concentration of isopropanol to generate at least one product with a higher concentration of isopropanol, at the same time, constantly recovering the extract agent, making the whole system able to quickly settle to the steady state of operation with low power consumption because of the extracting distillation unit having smaller size, greatly reducing operation risk without liquid left in the extract agent recovery unit, processing almost the input feed, improving overall efficiency, and further utilizing the vapor permeation film unit removing considerably little content of water from the organic solvent, thereby increasing the content of isopropanol up to more than 99.9%.

2. The Prior Arts

As well known, isopropanol (or called 2-propanol) is a common compound as a flammable liquid with strong odor at room temperature, and also a non-polar solvent capable of solving many substances. In particular, isopropanol is widely used as a cleaning agent because of quickly evaporating and non-toxic in contrast with other solvents. In the prior arts, a concentrating process for low concentration solvent is usually implemented by a plurality of, plate towers or packed towers (or so-called distillation towers) connected in series, and comprises steps of preliminarily removing water, then adding an extract agent to perform extracting distillation, and finally recovering the extract agent for re-use.

However, one shortcoming in the prior arts is that the settling time of operation is too long because of the larger size of the traditional distillation tower, and another shortcoming is that power consumption is huge. In particular, it is required to keep a large amount of sustaining liquid in the traditional distillation tower, and part of the liquid left at the bottom of the traditional distillation tower. As a result, it is easy to lead to additional risky situation while any accident event of operation happens around the distillation tower.

Therefore, it is greatly needed to provide a new system of concentrating and separating waste solvent mixture employing a distillation tower in collocation with an extracting distillation unit, an extract agent recovery unit, and a vapor permeation film unit connected in series for processing a waste solvent mixture with a lower concentration of isopropanol to generate at least one product with a higher concentration of isopropanol, at the same time, constantly recovering the extract agent, making the whole system able to quickly settle to the steady state of operation with low power consumption because of the extracting distillation unit having smaller size, greatly reducing operation risk without liquid left in the extract agent recovery unit, processing almost the input feed, improving overall efficiency, further utilizing the vapor permeation film unit removing considerably little content of water from the organic solvent, and increasing the content of isopropanol up to more than 99.9%, thereby overcoming the above problems in the prior arts.

SUMMARY OF THE INVENTION

The primary objective of the present invention is to provide a system of concentrating and separating waste solvent liquid, comprising a distillation tower, an extracting distillation unit, an extract agent recovery unit, and a vapor permeation film unit for implementing a concentrating process for low concentration solvent to generate an electronic level isopropanol product with ultra high concentration of isopropanol.

Specifically, the distillation tower is configured for receiving and processing a first input liquid through distillation and condensation to generate a distillation product and a distillation waste water. The distillation waste water is discharged through a bottom of the distillation tower, and the distillation product is transferred from a top of the distillation tower. In addition, the first input liquid contains a first input concentration of isopropanol, and the distillation product contains a distillation concentration of isopropanol higher than the first input concentration. Particularly, the first input concentration is equal to or higher than 5% by weight, and the distillation concentration is within 85 and 87.5% by weight, thereby achieving the effect of preliminarily increasing concentration. The above distillation product enters a first control valve so as to split into and transfer a first product, a first distillation concentrated product, and a second distillation concentrated product, and the first product is discharged for re-use.

More specifically, the extracting distillation unit is similar to the extract agent recovery unit in terms of structure.

Further, the extracting distillation unit accommodates a preset amount of the extract solvent like ethylene glycol, and is connected to the first control valve for receiving the first distillation concentrated product and a second input liquid. The second input liquid contains a second input concentration of isopropanol, and the second input concentration is equal to or higher than 80% by weight. In other words, the concentration of isopropanol in the second input liquid is considerably higher than the concentration of isopropanol in the first input liquid. In addition, a mixture of the first distillation concentrated product and the extract agent or a mixture of the extract agent and the second input liquid is treated through a process of extraction and distillation to generate an extract agent recovery liquid and an extract distillation concentrated product. The extract agent recovery liquid is discharged from a bottom of the extracting distillation unit, and the extract distillation concentrated product is discharged from a top of the extracting distillation unit. The extract agent recovery liquid comprises a recovery concentration of the extract agent. The extract distillation concentrated product contains an extract distillation concentration of isopropanol higher than the distillation concentration. In particular, the extract distillation concentration is equal to or higher than 99.5% by weight. That is, the extracting distillation unit achieves a further concentrating effect. Then, the extract distillation concentrated product is transferred to a second control valve, the second control valve splits the extract distillation concentrated product into a second product and an extract distillation liquid, and the second product is intended for re-use.

The extract agent recovery unit is connected to the extracting distillation unit and the distillation tower for receiving the extract agent recovery liquid from the extracting distillation unit. The extract agent recovery liquid is treated by the extract agent recovery unit to generate an extract agent reflow liquid and a recovery reflow liquid. The extract agent reflow liquid is discharged from a bottom of the extract agent recovery unit and then transferred to the extracting distillation unit, and the recovery reflow liquid is discharged from a top of the extract agent recovery unit. Further, the extract agent reflow liquid contains a reflow concentration of the extract agent, and the recovery reflow liquid contains a recovery reflow concentration of the extract agent lower than the extract agent reflow concentration. The recovery reflow liquid is directly transferred to the distillation tower or indirectly transferred to the distillation tower through a third control valve.

The vapor permeation film unit is connected to the first control valve and the second control valve for receiving the second distillation concentrated product, the extract distillation liquid, and a third input liquid. At least one of a third product, a fourth product, a fifth product, and a sixth product is generated by the vapor permeation film unit for re-use. At the same time, a vapor permeation waste water is discharged from a bottom of the vapor permeation film unit. The vapor permeation waste water is directly fed into the distillation tower, or indirectly transferred to the distillation tower through the third control valve. For example, the third input liquid contains a third input concentration of isopropanol, and the third input concentration is equal to or higher than 80% by weight. Further, the third product is generated through the distillation tower, the extracting distillation unit, and the vapor permeation film unit under control of the first control valve, the second control valve, and the third control valve when the first input liquid is fed but the second input liquid and the third input liquid are not fed, and the third product contains a concentration of isopropanol equal to or more than 99.9% by weight. The fourth product is generated through the distillation tower and the vapor permeation film unit under control of the first control valve, the second control valve, and the third control valve when the first input liquid is fed but the second input liquid and the third input liquid are not fed, and the fourth product contains a concentration of isopropanol equal to or more than 99.5% by weight. In addition, the fifth product is generated through the extracting distillation unit and the vapor permeation film unit under control of the second control valve and the third control valve when the second input liquid is fed but the first input liquid and the third input liquid are not fed, and the fifth product contains a concentration of isopropanol equal to or more than 99.5% by weight. More specifically, the sixth product is generated through the vapor permeation film unit when the third input liquid is directly fed into the vapor permeation film unit but the first input liquid and the second input liquid are not fed, and the sixth product contains a concentration of isopropanol equal to or more than 99.5% by weight.

Moreover, each of the extracting distillation unit and the extract agent recovery unit comprises moving plates, moving circulating loops, a gas input pipe, the liquid input pipes, static plates, static circulating loops, a gas output pipe, conducting pipes, a reflow pipe, liquid output pipes, a rotation axis, and a case body, and the case body enveloping the moving plates, the moving circulating loops, the gas input pipe, the liquid input pipes, the static plates, the static circulating loops, the gas output pipe, the conducting pipes, the reflow pipe, the liquid output pipes, and the rotation axis for implementing the effect of insulation and protection.

In the extracting distillation unit, the liquid input pipes are provided at a side of the extracting distillation unit for feeding the first distillation concentrated product, the second input liquid, and the extract agent reflow liquid; a gas output pipe is provided at the top of the extracting distillation unit for discharging a distillation vapor, and the distillation vapor condenses and forms a condensed liquid, a part of the condensed liquid feeds in the extracting distillation unit through a reflow pipe provided at the top of the extracting distillation unit, and the other part of the condensed liquid is discharged and serving as the extract distillation concentrated product; a liquid output pipe is provided at the bottom of the extracting distillation unit for discharging a part of a liquid left in the extracting distillation unit as the extract agent recovery liquid, the other part of the liquid left in the extracting distillation unit is further heated and evaporating to form an extract agent recovery vapor, the extract agent recovery vapor feeds in the extracting distillation unit through a gas input pipe provided at the bottom of the extracting distillation unit; each moving plate is horizontally provided and has a center through-hole; the moving circulating loops are provided on the moving plates; each static plate is horizontally provided and has a center through-hole; the static circulating loops are provided on the static plates; the conducting pipes penetrate the static plates and the moving plates; the rotation axis is vertically provided at a center of the extracting distillation unit.

Further, each of the moving plates is provided under the corresponding static plate, the rotation axis is inserted through the center through-holes of the moving plates and the static plates, the moving circulating loops and the static circulating loops forming a plurality of circulating channels for the first distillation concentrated product and the second input liquid pass through, each of the conducting pipes is configured close to the rotation axis to form a plurality of gas-liquid circulating channels to provide for the first distillation concentrated product, the second input liquid, and the extract agent reflow liquid to contact and further pass through.

The extract agent recovery unit is similar to the extracting distillation unit. In the extract agent recovery unit, the liquid input pipes are provided at a side of the extract agent recovery unit for feeding the extract agent recovery liquid; the gas output pipe is provided at the top of the extract agent recovery unit for discharging a distillation vapor, and the distillation vapor condenses and forms a condensed liquid, a part of the condensed liquid feeding the extract agent recovery unit through a reflow pipe provided at the top of the extract agent recovery unit, the other part of the condensed liquid discharged and serving as the recovery reflow liquid; the liquid output pipe is provided at the bottom of the extract agent recovery unit for discharging a part of a liquid left in the extract agent recovery unit as the extract agent reflow liquid, the other part of the liquid left in the extract agent recovery unit is further heated and evaporates to form an extract agent reflow vapor, and the extract agent reflow vapor feeds in the extract agent recovery unit through a gas input pipe provided at the bottom of the extract agent recovery unit; each moving plate and each static plate are horizontally provided and have a center through-hole; the conducting pipes penetrate the static plates and the moving plates; a rotation axis is vertically provided at a center of the extract agent recovery unit; the moving circulating loops are provided on the moving plates; and the static circulating loops are provided on the static plates.

In addition, each of the moving plates is provided under the corresponding static plate, and the rotation axis is inserted through the center through-holes of the moving plates and the static plates. In particular, the moving circulating loops and the static circulating loops form a plurality of circulating channels for the extract agent recovery liquid to pass through.

Therefore, the present invention employs the distillation tower in collocation with the extracting distillation unit, the extract agent recovery unit, and the vapor permeation film unit connected in series to achieve the feature of increasing the concentration of isopropanol from a very low value up to ultra a high value, and at the same time, constantly recovers the extract agent during the operation of the system, furthermore the extracting distillation unit having a smaller size such that the system quickly settle down and power consumption is greatly reduced.

Further, since the extracting distillation unit does not need to keep any liquid, risk during operation is reduced, and the system is able to process all the input liquid so as to greatly improve overall efficiency of operation. In particular, the investment on the operation facilities of the present invention is reduced, the expenses of land and factory are also decreased, and operational power consumption is kept low, leading to competitive operation cost.

Moreover, another object of the present invention is to provide a system of concentrating and separating waste solvent liquid, comprising an ultra gravitational bed unit, an extracting distillation unit, an extract agent recovery unit, and a vapor permeation film unit for implementing a concentrating process for low concentration solvent to generate an electronic level isopropanol product with ultra high concentration of isopropanol, and generating a seventh product, a eighth product, a ninth product, a tenth product, a eleventh product, and a twelfth product to replace the first product, the second product, the third product, the fourth product, the fifth product, and the sixth product mentioned above, respectively. It should be noted that the ultra gravitational bed unit is similar to the extracting distillation unit and the extract agent recovery unit in structure, and since the features of the extracting distillation unit and the extract agent recovery unit are described in detail, only the ultra gravitational bed unit is illustrated hereinafter.

More specifically, the ultra gravitational bed unit is intended for receiving and processing a first input liquid through distillation and condensation to generate a distillation product and a distillation waste water. The distillation waste water is discharged through a bottom of the ultra gravitational bed unit, and the distillation product is transferred from a top of the ultra gravitational bed unit. The first input liquid contains a first input concentration of isopropanol, and the distillation product contains a distillation concentration of isopropanol higher than the first input concentration. In particular, the first input concentration is equal to or higher than 5% by weight, and the distillation concentration within 85 and 87.5% by weight. The distillation product enters a first control valve to split into and transfer the seventh product, a first distillation concentrated product, and a second distillation concentrated product, and the seventh product is discharged for re-use.

Accordingly, the ultra gravitational bed unit comprises moving plates, moving circulating loops, a gas input pipe, the liquid input pipes, static plates, static circulating loops, a gas output pipe, conducting pipes, a reflow pipe, liquid output pipes, a rotation axis, and a case body, and the case body envelopes the moving plates, the moving circulating loops, the gas input pipe, the liquid input pipes, the static plates, the static circulating loops, the gas output pipe, the conducting pipes, the reflow pipe, the liquid output pipes, and the rotation axis for implementing the effect of insulation and protection.

In the ultra gravitational bed unit, the liquid input pipes are provided at a side of the ultra gravitational bed unit for feeding the first input liquid, the recovery reflow liquid, and the vapor permeation waste water; the gas output pipe is provided at the top of the ultra gravitational bed unit for discharging a distillation vapor, the distillation vapor condenses and forms a condensed liquid, a part of the condensed liquid feeds the ultra gravitational bed unit through a reflow pipe provided at the top of the ultra gravitational bed unit, and the other part of the condensed liquid is discharged and serving as the distillation product; the liquid output pipe is provided at the bottom of the ultra gravitational bed unit for discharging a part of a liquid left in the ultra gravitational bed unit as the evaporation waste water, the other part of the liquid left in the ultra gravitational bed unit is further heated and evaporates to form an vapor, and the vapor then feeds the ultra gravitational bed unit through a gas input pipe provided at the bottom of the ultra gravitational bed unit; each moving plate is horizontally provided and has a center through-hole; the moving circulating loops are provided on the moving plates; each static plate is horizontally provided and has a center through-hole; the static circulating loops are provided on the static plates; the conducting pipes penetrate the static plates and the moving plates; the rotation axis is vertically provided at a center of the ultra gravitational bed unit.

Additionally, each moving plates is provided under the corresponding static plate, the rotation axis is inserted through the center through-holes of the moving plates and the static plates, the moving circulating loops and the static circulating loops form a plurality of circulating channels for the first input liquid, the recovery reflow liquid, and the vapor permeation waste water to contact and further pass through.

Overall, the ultra gravitational bed unit provides the same feature as the distillation tower provides, and is substantially able to replace the above distillation tower to fully collocate with the extracting distillation unit, the extract agent recovery unit, and the vapor permeation film unit for generating the seventh product, the eighth product, the ninth product, the tenth product, the eleventh product, and the twelfth product with different concentrations of isopropanol according to the demand of the customer. Since the seventh product, the eighth product, the ninth product, the tenth product, the eleventh product, and the twelfth product are able to replace the first product, the second product, the third product, the fourth product, the fifth product, and the sixth product, respectively, the related technical description is thus omitted hereinafter.

Accordingly, the ultra gravitational bed unit does not retain any liquid so as to reduce operational risk, and the system is able to process all the input liquid to greatly improve overall efficiency of operation. The present invention thus greatly decreases the investment on the operation facilities, the expenses of land and factory, and operational power consumption, thereby reducing overall cost.

BRIEF DESCRIPTION OF THE DRAWINGS

The present invention can be understood in more detail by reading the subsequent detailed description in conjunction with the examples and references made to the accompanying drawings, wherein.

DETAILED DESCRIPTION OF THE PREFERRED EMBODIMENT

The present invention may be embodied in various forms and the details of the preferred embodiments of the present invention will be described in the subsequent content with reference to the accompanying drawings. The drawings (not to scale) show and depict only the preferred embodiments of the invention and shall not be considered as limitations to the scope of the present invention. Modifications of the shape of the present invention shall to be considered to be within the spirit of the present invention.

Figure 1:
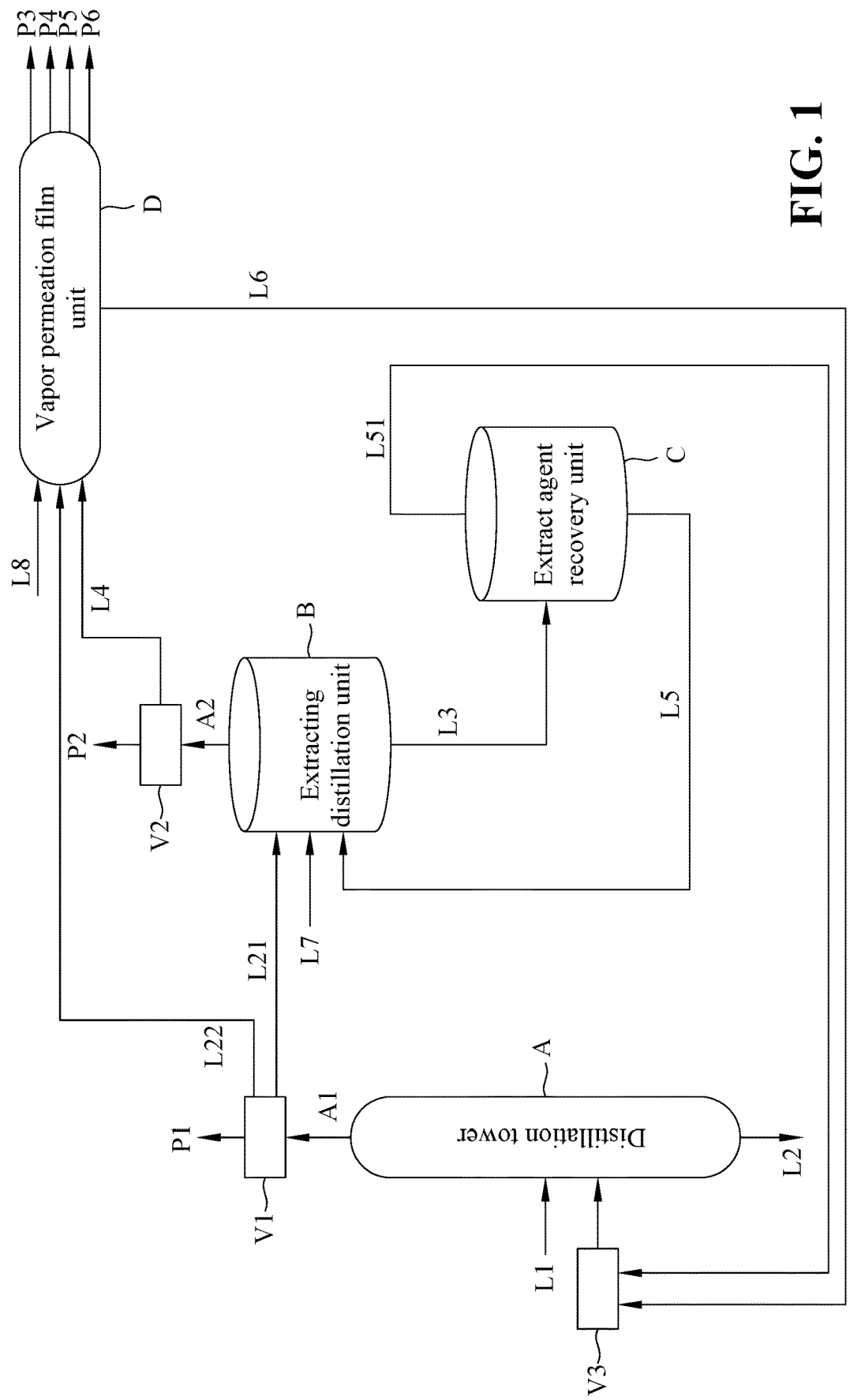
FIG. 1 is a view showing the system of concentrating and separating waste solvent liquid according to the first embodiment of the present invention.

Please refer to FIG. 1 illustrating the view showing the system of concentrating and separating waste solvent liquid according to the first embodiment of the present invention. As shown in FIG. 1, the system of concentrating and separating waste solvent liquid according to the first embodiment of the present invention comprises a distillation tower A, an extracting distillation unit B, an extract agent recovery unit C, and a vapor permeation film unit D for implementing a concentrating process on the low isopropanol concentration liquid to generate an electronic level product with ultra high concentration of isopropanol.

Specifically, the distillation tower A is configured for receiving and processing a first input liquid L1 through distillation and condensation to generate a distillation product A1 and a distillation waste water L2. The distillation waste water L2 is discharged through a bottom of the distillation tower A, and the distillation product A1 is transferred from a top of the distillation tower A. The first input liquid L1 contains a first input concentration of isopropanol, and the distillation product A1 contains a distillation concentration of isopropanol higher than the first input concentration. Particularly, the first input concentration is equal to or higher than 5% by weight, and the distillation concentration is within 85 and 87.5% by weight such that the distillation tower A achieves the effect of preliminarily increasing concentration. The above distillation product A1 then enters a first control valve V1 so as to split into and transfer a first product P1, a first distillation concentrated product L21, and a second distillation concentrated product L22, and the first product is discharged for re-use.

It should be noted that the extracting distillation unit B and the extract agent recovery unit C are similar in overall structure.

Further, the extracting distillation unit B substantially accommodates a preset amount of the extract solvent or agent and is connected to the first control valve V1 for receiving the first distillation concentrated product L21. More specifically, the first distillation concentrated product L21 is mixed with the extract solvent in the extracting distillation unit B, and then treated through a process of extraction and distillation to generate an extract agent recovery liquid L3 and an extract distillation concentrated product A2. The extract agent recovery liquid L3 is discharged from a bottom of the extracting distillation unit B, and the extract distillation concentrated product A2 is discharged from a top of the extracting distillation unit B. The extract agent recovery liquid L3 comprises a recovery concentration of the extract agent, and the extract distillation concentrated product A2 contains an extract distillation concentration of isopropanol higher than the distillation concentration. In particular, the extract distillation concentration is equal to or higher than 99.5% by weight. That is, the extracting distillation unit B achieves a further concentrating effect. Then, the extract distillation concentrated product A2 is transferred to a second control valve V2, and the second control valve V2 splits the extract distillation concentrated product A2 into a second product P2 and an extract distillation liquid L4. The second product is intended for re-use.

In addition, a second input liquid L7 may further feed the extracting distillation unit B. The second input liquid L7 contains a second input concentration of isopropanol equal to or higher than 80% by weight. In other words, the concentration of isopropanol in the second input liquid L7 is considerably higher than the concentration of isopropanol in the first input liquid L1. Thus, a mixture of the first distillation concentrated product L21 and the extract agent or a mixture of the extract agent and the second input liquid L7 is treated through a process of extraction and distillation to generate the extract agent recovery liquid L3 and the extract distillation concentrated product A2. For instance, the second input liquid L7 is supplied by other isopropanol sources like another concentrating system.

Similarly, the extract agent recovery unit C is connected to the extracting distillation unit B and the distillation tower A for receiving the extract agent recovery liquid L3 from the extracting distillation unit B. The extract agent recovery liquid L3 is treated by the extract agent recovery unit C to generate an extract agent reflow liquid L5 and a recovery reflow liquid L51. The extract agent reflow liquid L5 is discharged from a bottom of the extract agent recovery unit C and then transferred to the extracting distillation unit B, and the recovery reflow liquid L5 is discharged from a top of the extract agent recovery unit C. Further, the extract agent reflow liquid L5 contains a reflow concentration of the extract agent, and the recovery reflow liquid L51 contains a recovery reflow concentration of the extract agent lower than the reflow concentration. The recovery reflow liquid L51 is directly transferred to the distillation tower A or indirectly transferred to the distillation tower A through a third control valve V3. Thus, the primary effect provided by the extract agent recovery unit C is to constantly recover the extract agent such that the extract agent is recycled and re-used during the whole operation of the system. For example, the extract agent comprises ethylene glycol.

Further, the vapor permeation film unit D is connected to the first control valve V1 and the second control valve V2 for receiving the second distillation concentrated product L22 and the extract distillation liquid L4, or further receiving a third input liquid L8. At least one of a third product P3, a fourth product P4, a fifth product P5, and a sixth product P6 is generated by the vapor permeation film unit D for re-use. At the same time, a vapor permeation waste water L6 is discharged from a bottom of the vapor permeation film unit D. The vapor permeation waste water L6 is directly fed into the distillation tower A, or indirectly transferred to the distillation tower A through the third control valve V3. For instance, the third input liquid L8 contains a third input concentration of isopropanol, and the third input concentration is equal to or higher than 80% by weight. Thus, the primary function is to further increase the concentration of isopropanol.

Further, the third product P3 is generated through the distillation tower A, the extracting distillation unit B, and the vapor permeation film unit D under control of the first control valve V1, the second control valve V2, and the third control valve V3 when the first input liquid L1 is fed but the second input liquid L7 and the third input liquid L8 are not fed, and the third product P3 contains a concentration of isopropanol equal to or more than 99.9% by weight. The fourth product P4 is generated through the distillation tower A and the vapor permeation film unit D under control of the first control valve V1, the second control valve V2, and the third control valve V3 when the first input liquid L1 is fed but the second input liquid L7 and the third input liquid L8 are not fed, and the fourth product P4 contains a concentration of isopropanol equal to or more than 99.5% by weight. In addition, the fifth product P5 is generated through the extracting distillation B unit and the vapor permeation film unit D under control of the second control valve V2 and the third control valve V3 when the second input liquid L7 is fed but the first input liquid L1 and the third input liquid L8 are not fed, and the fifth product P5 contains a concentration of isopropanol equal to or more than 99.5% by weight. More specifically, the sixth product P6 is generated through the vapor permeation film unit D when the third input liquid L8 is directly fed into the vapor permeation film unit D but the first input liquid L1 and the second input liquid L8 are not fed to the system, and the sixth product P6 contains a concentration of isopropanol equal to or more than 99.5% by weight.

Figure 2:
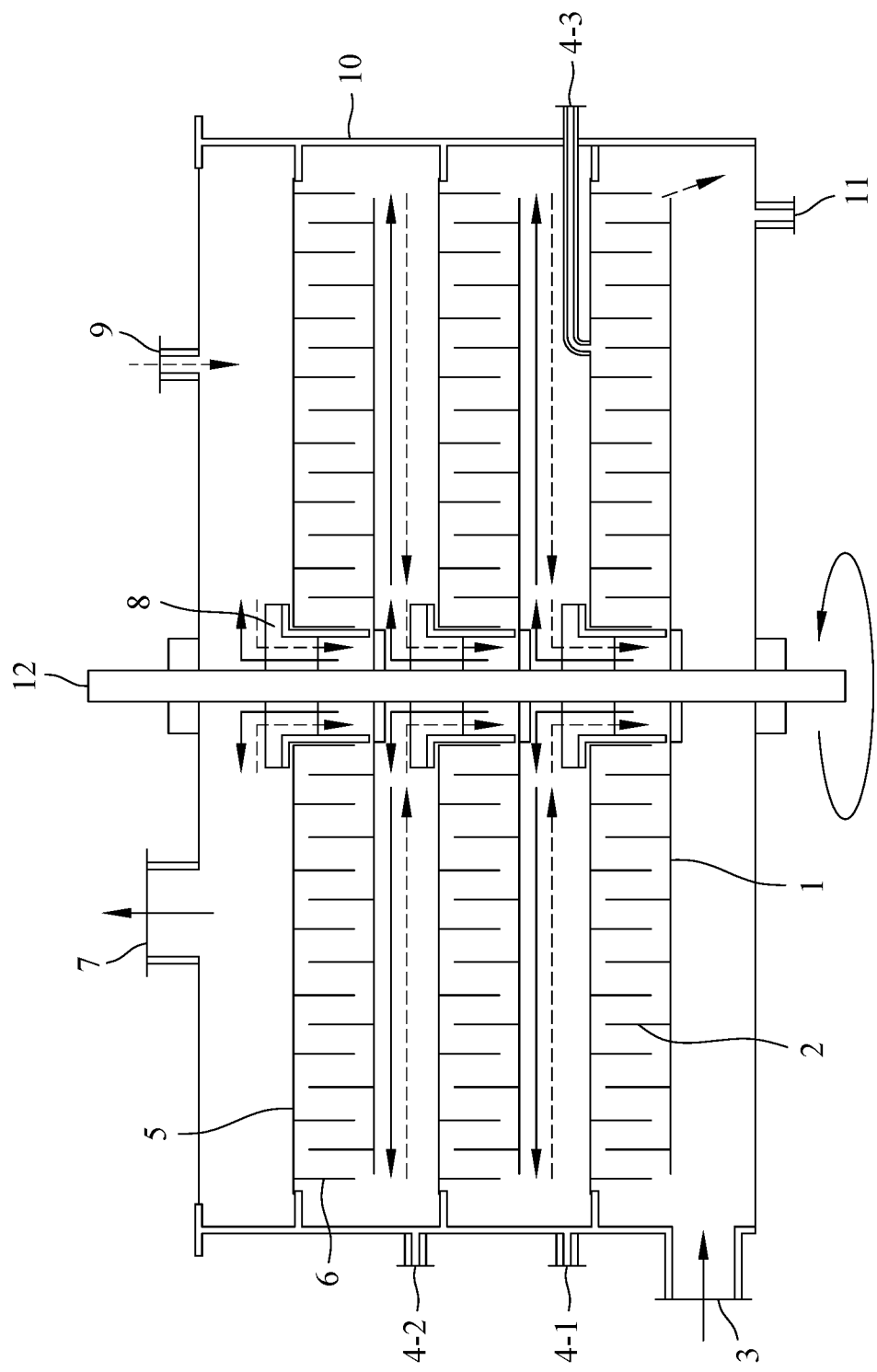
FIG. 2 is a view showing the extracting distillation unit or the extract agent recovery unit of the system according to the first embodiment of the present invention.

To further describe the feature of the present invention, refer to FIG. 2 illustrating the extracting distillation unit, the extract agent recovery unit or the ultra gravitational bed unit of the system according to the first embodiment of the present invention. Since the extracting distillation unit B and the extract agent recovery unit C are similar in structure, the feature about the extracting distillation unit B is described in detail hereinafter.

More specifically, the extracting distillation unit B comprises a plurality of moving plates 1, a plurality of moving circulating loops 2, a gas input pipe 3, a plurality of liquid input pipes 4-1, 4-2. 4-3, a plurality of static plates 5, a plurality of static circulating loops 6, a gas output pipe 7, a plurality of conducting pipes 8, a reflow pipe 9, a plurality of liquid output pipes 11, a rotation axis 12, and a case body 10 enveloping the moving plates 1, the moving circulating loops 2, the gas input pipe 3, the liquid input pipes 4-1, 4-2, 4-3, the static plates 5, the static circulating loops 6, the gas output pipe 7, the conducting pipes 8, the reflow pipe 9, the liquid output pipes 11, and the rotation axis 12 for implementing the effect of insulation and protection.

Further in the extracting distillation unit B, the liquid input pipes 4-1, 4-2. 4-3 are provided at a side of the extracting distillation unit B for feeding the first distillation concentrated product L21, the second input liquid L7, and the extract agent reflow liquid L5. The gas output pipe 7 is provided at the top of the extracting distillation unit B for discharging a distillation vapor, and the distillation vapor condenses and forms a condensed liquid, a part of the condensed liquid feeds in the extracting distillation unit B through a reflow pipe 9 provided at the top of the extracting distillation unit B, and the other part of the condensed liquid is discharged and serving as the extract distillation concentrated product A2. The liquid output pipe 11 is provided at the bottom of the extracting distillation unit B for discharging a part of a liquid left in the extracting distillation unit B as the extract agent recovery liquid L3. The other part of the liquid left in the extracting distillation unit B is further heated and evaporating to form an extract agent recovery vapor, the extract agent recovery vapor feeds the extracting distillation unit B through a gas input pipe 3 at the bottom of the extracting distillation unit B. Each moving plate 1 and each static plate 5 are horizontally provided and have a center through-hole. The moving circulating loops 2 are provided on the moving plates 1; the static circulating loops 6 are provided on the static plates 5; the conducting pipes 8 penetrate the static plates 5 and the moving plates 1; and the rotation axis 12 is vertically provided at a center of the extracting distillation unit B. More specifically, each of the moving plates 1 is provided under the corresponding static plate 5, the rotation axis 12 is inserted through the center through-holes of the moving plates 1 and the static plates 5, the moving circulating loops 2 and the static circulating loops 6 form a plurality of circulating channels for gas and liquid to contact.

Accordingly, refer to FIG. 2 again for describing the extract agent recovery unit C.

The extract agent recovery unit C similarly comprises a plurality of moving plates 1, a plurality of moving circulating loops 2, a gas input pipe 3, a plurality of liquid input pipes 4-1, 4-2. 4-3, a plurality of static plates 5, a plurality of static circulating loops 6, a gas output pipe 7, a plurality of conducting pipes 8, a reflow pipe 9, a plurality of liquid output pipes 11, a rotation axis 12, and a case body 10 enveloping the moving plates 1, the moving circulating loops 2, the gas input pipe 3, the liquid input pipes 4-1, 4-2, 4-3, the static plates 5, the static circulating loops 6, the gas output pipe 7, the conducting pipes 8, the reflow pipe 9, the liquid output pipes 11, and the rotation axis 12 for implementing the effect of insulation and protection. Further, the liquid input pipes 4-1, 4-2. 4-3 of the extract agent recovery unit C are provided at a side of the extract agent recovery unit C for feeding the extract agent recovery liquid L3; the gas output pipe 7 is provided at the top of the extract agent recovery unit C for discharging a distillation vapor, and the distillation vapor condenses and forms a condensed liquid, a part of the condensed liquid feeding the extract agent recovery unit C through a reflow pipe 9 provided at the top of the extract agent recovery unit C, the other part of the condensed liquid discharged and serving as the recovery reflow liquid L51; the liquid output pipe 11 is provided at the bottom of the extract agent recovery unit C for discharging a part of a liquid left in the extract agent recovery unit C as the extract agent reflow liquid L5, the other part of the liquid left in the extract agent recovery unit C is further heated and evaporates to form an extract agent reflow vapor, and the extract agent reflow vapor feeds in the extract agent recovery unit C through a gas input pipe at the bottom of the extract agent recovery unit C; each moving plate 1 and each static plate 5 are horizontally provided and have a center through-hole; the conducting pipes 8 penetrate the static plates 5 and the moving plates 1; a rotation axis 12 is vertically provided at a center of the extract agent recovery unit C; the moving circulating loops 2 are provided on the moving plates 1; and the static circulating loops 6 are provided on the static plates 5. The moving circulating loops 2 and the static circulating loops 6 form a plurality of circulating channels for gas and liquid to contact.

The above vapor permeation film unit D is widely used in the prior arts, and only simple feature is described hereinafter. Specifically, the vapor permeation film unit D primarily provides a mechanism of dissolution and diffusion for increasing the concentration of isopropanol. In general, the vapor permeation film unit D is provided with a heating evaporator and a vapor permeation film (not shown) for implementing separation of solvent and water to effectively separate water and solvent. The heating evaporator is employed to heat the second distillation concentrated product L22 and the extract distillation liquid L4 to evaporate and form a heated vapor comprising water vapor and isopropanol, the heated vapor flows through a shell side of the vapor permeation film unit D, and the water vapor in the heated vapor diffuses and further penetrates the vapor permeation film to arrive at and be discharged from a pipe side of the vapor permeation film unit D through the mechanism of dissolution and diffusion. Further, isopropanol in the heated vapor is left in the shell side so as to implement separation of water and isopropanol. More specifically, the vapor permeation film comprises at least one of Polyvinyl alcohol (PVA), Polyacrylamide (PAM), Polyacrylonitrile (PAN), Cellulose acetate (CA), 4 (Nylon-4), Polysulfone (PSU), Polyethersulfone (PES), Chitosan, Polyimide (PI), a ceramic film, a metal film, molecular screen film, a carbon film, and an organic-inorganic composite film, and the organic-inorganic composite film employs an inorganic film as a supporting layer, and an organic film stacked on the inorganic film as a selective layer.

It should be noted that the vapor permeation film unit D described above is only an illustrative example for clear explanation of the features of the present invention, and not intended to limit the scope of the present invention. In other words, other schemes to provide the mechanism of dissolution and diffusion are also covered by the present invention.

Figure 3:
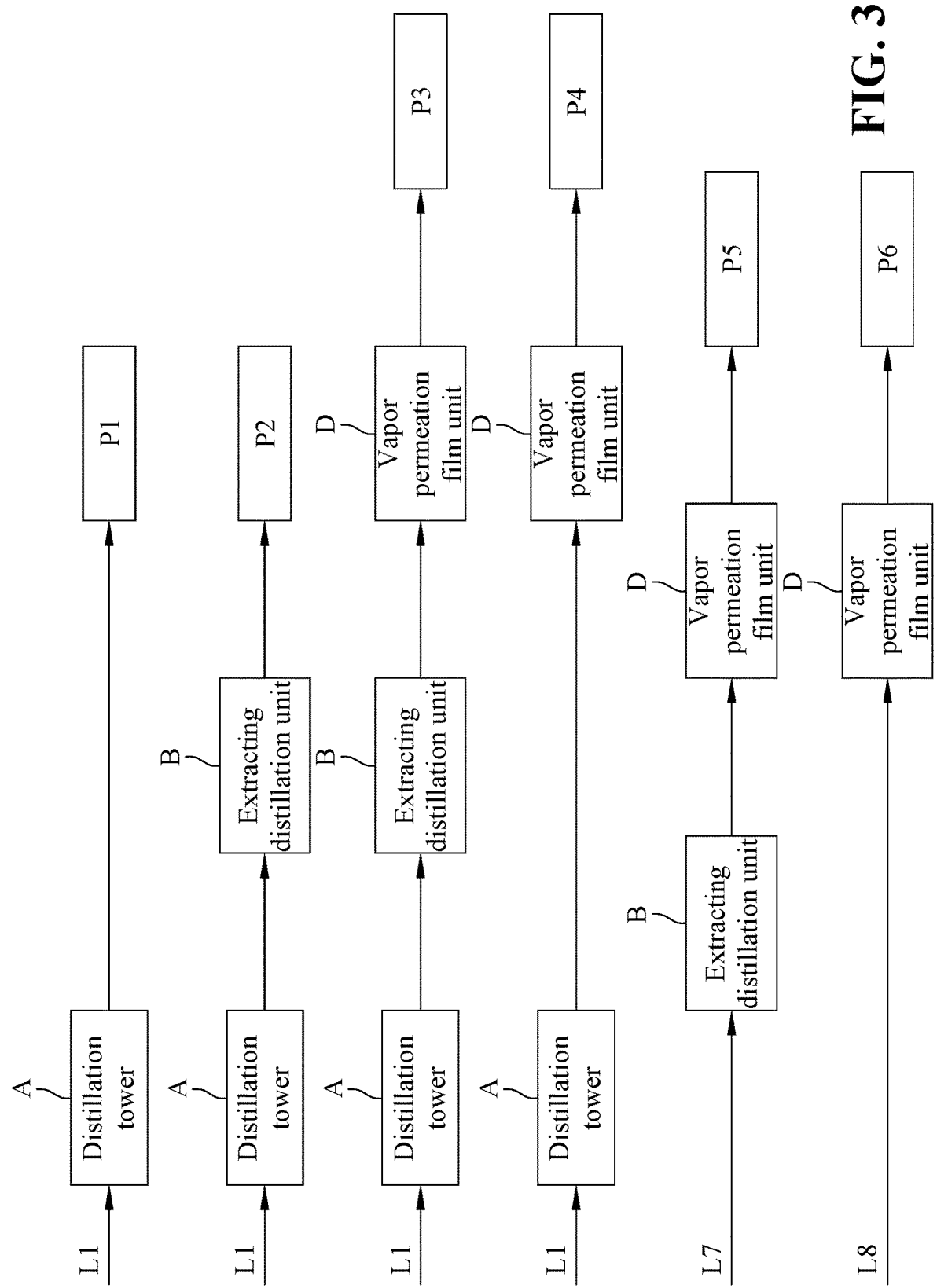
FIG. 3 is a simplified view showing the system according to the first embodiment of the present invention.

Overall, the key aspect of the first embodiment of the present invention for the first product P1, the second product P2, the third product P3, the fourth product P4, the fifth product P5, and the sixth product P6 is clearly summarized and illustrated in FIG. 3. The first embodiment of the present invention employs the traditional distillation tower A in collocation with the extracting distillation unit B and the extract agent recovery unit C connected in series as two new deices, and further utilizes the vapor permeation film unit D connected to the end part of the extracting distillation unit B for implementing the concentrating process on the low isopropanol liquid to generate various product with different concentration of isopropanol according to the demand of the customer, including the first product P1, the second product P2, the third product P3, the fourth product P4, the fifth product P5, and the sixth product P6. For example, the first product P1 with the isopropanol concentration of 85% to 87.5% by weight is directly generated by the traditional distillation tower A, the second product P2 with the isopropanol concentration equal to or higher than 99.5% by weight is generated through the extracting distillation unit B, and particularly, the third product P3 with the isopropanol concentration equal to or higher than 99.9% by weight is generated from the first input liquid L1 through the distillation tower A, the extracting distillation unit B, and the vapor permeation film unit D under control of the first control valve V1, the second control valve V2, and the third control valve V3, or the fourth product P4 with the isopropanol concentration equal to or higher than 99.5% by weight is generated from the first input liquid L1 through the distillation tower A and the vapor permeation film unit D, or the fifth product P5 with the isopropanol concentration equal to or higher than 99.5% by weight is generated from the second input liquid L7 through the extracting distillation unit B and the vapor permeation film unit D. In addition, the sixth product P6 with the isopropanol concentration equal to or higher than 99.5% by weight is directly generated from the third input liquid L8 by the vapor permeation film unit D.

Further, the first input liquid L1 is fed and then circulates through the moving circulating loops 2 within the moving plates 1 and the static circulating loops 6 within the static circulating loops 6. In particular, the first input liquid L1 sprinkles and forms little droplets due to centrifugal force, and the fall down on the moving plates 1 due to gravity. The above process is repeated. At the same time, the gas component enters from the bottom, and flows in a counter direction and a relative velocity with respect to the liquid component such that liquid and gas circulating through the moving circulating loops 2 within the moving plates 1 and the static circulating loops 6 within the static circulating loops 6 are able to fully contact. Thus, when the flow rate of gas increases, the accumulated amount of liquid decreases. As a result, the thickness of the liquid film on each of the static circulating loops 6 decreases, and mass transfer resistance between gas and liquid reduces, thereby greatly increasing contact area of phase interface and enhancing the mass transfer process.

Furthermore, the first input liquid L1 with the low concentration of isopropanol is preliminarily concentrated by the distillation tower, and a mixture with the isopropanol concentration of 87.7% by weight or usually called azoetrope is then formed by mixing with the extract agent. The azoetrope is processed through the steps of evaporation, condensation, and collection to evaporate and discharge the substance with a low boiling point to the top of the distillation tower, and the substance with a high boiling point still remaining liquid phase is discharged to the bottom of the distillation tower. Thus, the effect of separating solvent from other substances is implemented. At that time, the product generated is further processed through the vapor distillation unit by adding the extract agent like ethylene glycol such that isopropanol is separated from the azoetrope, and the product having much higher concentration isopropanol is thus generated. Additionally, the extract agent added is recovered from the extract agent recovery unit, and constantly re-use during the whole operation. Also, the system employs the vapor permeation film unit to saves power consumption without heating and without adding any third component or chemical so as to effectively separate considerably little water and organic solvent and greatly increase the concentration of isopropanol higher than 99.9% by weight and reduce water content below 1000 ppm.

Figure 4:
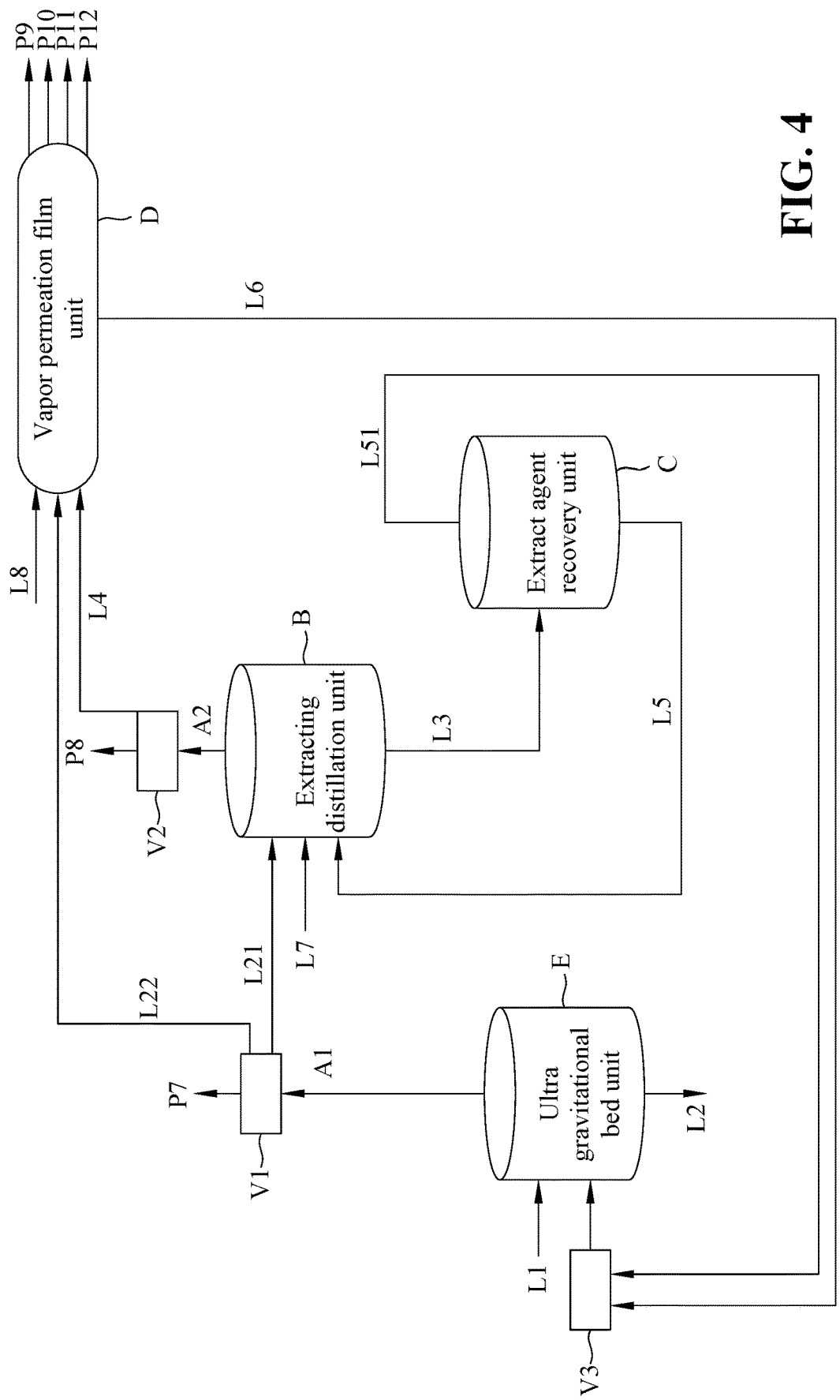
FIG. 4 is a view showing the system of concentrating and separating waste solvent liquid according to the second embodiment of the present invention.

Further refer to FIG. 4 illustrating the system of concentrating and separating waste solvent liquid according to the second embodiment of the present invention. As shown in FIG. 4, the system of concentrating and separating waste solvent liquid according to the second embodiment of the present invention generally comprises an ultra gravitational bed unit E, an extracting distillation unit B, an extract agent recovery unit C, and a vapor permeation film unit D for implementing a concentrating process on the low isopropanol concentration liquid up to an electronic level product with ultra high concentration of isopropanol, and generating the seventh product P7, the eighth product P8, the ninth product P9, the tenth product P10, the eleventh product P11, and the twelfth product P12 to replace the first product P1, the second product P2, the third product P3, the fourth product P4, the fifth product P5, and the sixth product P6 as mentioned above, respectively, to provide the same features. The ultra gravitational bed unit E is similar to the extracting distillation unit B and the extract agent recovery unit C in terms of structure, and since the technical aspects of the extracting distillation unit B, the extract agent recovery unit C, and vapor permeation film unit D are described in detail, only the specific feature provided by the ultra gravitational bed unit E is described hereinafter.

Specifically, the ultra gravitational bed unit E is intended for receiving the first input liquid L1 through distillation and condensation to generate the distillation product A1 and the distillation waste water L2. The distillation waste water L2 is discharged through a bottom of the ultra gravitational bed unit E, and the distillation product A1 is transferred from a top of the ultra gravitational bed unit E. The distillation product A1 then enters the first control valve V1 so as to split into and transfer the seventh product P7, the first distillation concentrated product L21, and the second distillation concentrated product L22, and the seventh product P7 is discharged for re-use.

Accordingly, the ultra gravitational bed unit E also comprises a plurality of moving plates 1, a plurality of moving circulating loops 2, a gas input pipe 3, a plurality of liquid input pipes 4-1, 4-2, 4-3, a plurality of static plates 5, a plurality of static circulating loops 6, a gas output pipe 7, a plurality of conducting pipes 8, a reflow pipe 9, a plurality of liquid output pipes 11, a rotation axis 12, and a case body 10 enveloping the moving plates 1, the moving circulating loops 2, the gas input pipe 3, the liquid input pipes 4-1, 4-2, 4-3, the static plates 5, the static circulating loops 6, the gas output pipe 7, the conducting pipes 8, the reflow pipe 9, the liquid output pipes 11, and the rotation axis 12 for implementing the effect of insulation and protection.

In the ultra gravitational bed unit E, the liquid input pipes 4-1, 4-2, 4-3 are provided at a side of the ultra gravitational bed unit E for feeding the first input liquid L1, the recovery reflow liquid L51, and the vapor permeation waste water L6. The gas output pipe 7 is provided at the top of the ultra gravitational bed unit E for discharging a distillation vapor, and the distillation vapor condenses and forms a condensed liquid, a part of the condensed liquid feeds the ultra gravitational bed unit E through a reflow pipe 9 provided at the top of the ultra gravitational bed unit E, and the other part of the condensed liquid is discharged and serving as the distillation product A1. The liquid output pipe 11 is provided at the bottom of the ultra gravitational bed unit E for discharging a part of a liquid left in the ultra gravitational bed unit E as the evaporation waste water L2. The other part of the liquid left in the ultra gravitational bed unit E is further heated, evaporating, and feeds in the ultra gravitational bed unit E through a gas input pipe 3 provided at the bottom of the ultra gravitational bed unit E. Each moving plate 1 and each static plate 5 are horizontally provided and have a center through-hole. The moving circulating loops 2 are provided on the moving plates 1; the static circulating loops 6 are provided on the static plates 5; the conducting pipes 8 penetrate the static plates 5 and the moving plates 1; and the rotation axis 12 is vertically provided at a center of the ultra gravitational bed unit E. More specifically, each of the moving plates 1 is provided under the corresponding static plate 5, the rotation axis 12 is inserted through the center through-holes of the moving plates 1 and the static plates 5, the moving circulating loops 2 and the static circulating loops 6 form a plurality of circulating channels for gas and liquid to contact.

Figure 5:
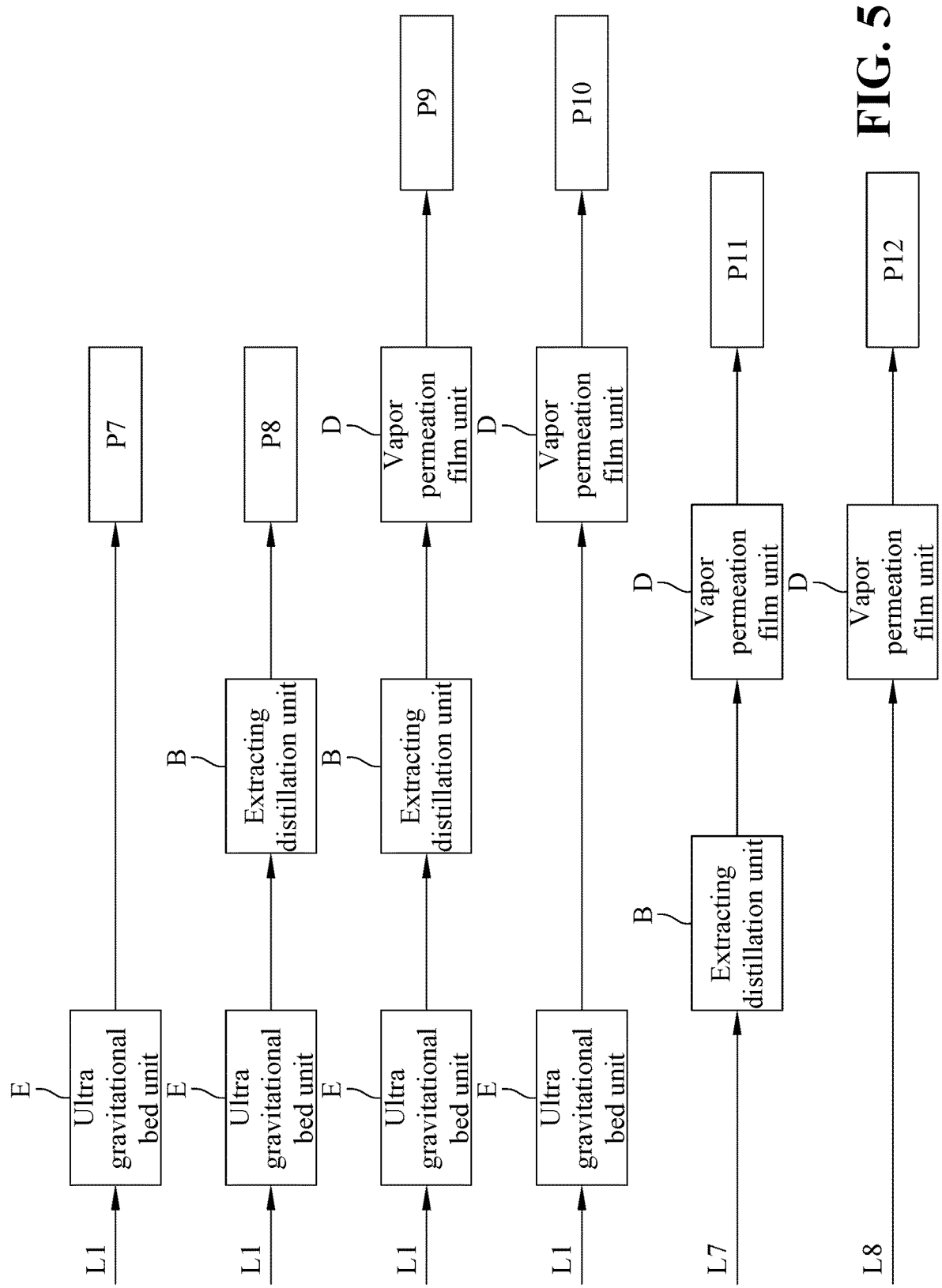
FIG. 5 is a simplified view showing the system according to the second embodiment of the present invention.

Overall, the ultra gravitational bed unit E provides the same feature as the distillation tower A provides, and is able to fully replace the distillation tower A in the first embodiment for collocating with the extracting distillation unit B, the extract agent recovery unit C, and the vapor permeation film unit D, thereby generating g the seventh product P7, the eighth product P8, the ninth product P9, the tenth product P10, the eleventh product P11, and the twelfth product P12 with different concentrations of isopropanol according to the demand of the customer as shown in FIG. 5 to replace the first product P1, the second product P2, the third product P3, the fourth product P4, the fifth product P5, and the sixth product P6 generated in the first embodiment, respectively.

From the above mention, the aspect of the second embodiment of the present invention is that the ultra gravitational bed unit is employed to collocate with the extracting distillation unit, the extract agent recovery unit, and the vapor permeation film unit for implementing the concentrating process on the low isopropanol concentration liquid so as to generate the high isopropanol concentration liquid, and additionally, the extract agent is constantly recovered and re-use during the whole operation of the system, plus the smaller size of the extracting distillation unit, such that the settling time of the system is considerably short and power consumption is also greatly reduced.

Although the present invention has been described with reference to the preferred embodiments, it will be understood that the invention is not limited to the details described thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A system of concentrating and separating waste solvent liquid, comprising:

a distillation tower for receiving and processing a first input liquid through distillation and condensation to generate a distillation product and a distillation waste water, the distillation waste water discharged through a bottom of the distillation tower, the distillation product transferred from a top of the distillation tower, the first input liquid containing a first input concentration of isopropanol, the distillation product containing a distillation concentration of isopropanol higher than the first input concentration, the first input concentration equal to or higher than 5% by weight of the first input liquid, the distillation concentration within 85 to 87.5% by weight of the first input liquid, the distillation product entering a first control valve to split into and transfer a first product, a first distillation concentrated product, and a second distillation concentrated product, the first product being discharged for re-use;

an extracting distiller, which is configured to accommodate an extract agent, the extract agent comprising ethylene glycol, the extracting distiller connected to the first control valve for receiving the first distillation concentrated product and a second input liquid, the second input liquid containing a second input concentration of isopropanol, the second input concentration equal to or higher than 80% by weight of the second input liquid, a mixture of the first distillation concentrated product and the extract agent or a mixture of the extract agent and the second input liquid treated through a process of extraction and distillation to generate an extract agent recovery liquid and an extract distillation concentrated product, the extract agent recovery liquid discharged from a bottom of the extracting distiller, the extract agent recovery liquid comprising a recovery concentration of the extract agent, the extract distillation concentrated product containing an extract distillation concentration of isopropanol higher than the distillation concentration, the extract distillation concentration equal to or higher than 99.5% by weight of the extract agent recovery liquid, the extract distillation concentrated product discharged from a top of the extracting distiller and then transferred to a second control valve, the second control valve splitting the extract distillation concentrated product into a second product and an extract distillation liquid, the second product being for re-use;

an extract agent recover, which is connected to the extracting distiller and the distillation tower for receiving the extract agent recovery liquid from the extracting distiller, the extract agent recovery liquid treated by the extract agent recover to generate an extract agent reflow liquid and a recovery reflow liquid, the extract agent reflow liquid discharged from a bottom of the extract agent recover and transferred to the extracting distiller, the recovery reflow liquid discharged from a top of the extract agent recover, the extract agent reflow liquid containing a reflow concentration of the extract agent, the recovery reflow liquid containing a recovery reflow concentration of the extract agent lower than the reflow concentration, the recovery reflow liquid directly transferred to the distillation tower or indirectly transferred to the distillation tower through a third control valve; and a vapor permeation film, which is connected to the first control valve and the second control valve for receiving the second distillation concentrated product, the extract distillation liquid, and a third input liquid, at least one of a third product, a fourth product, a fifth product, and a sixth product being generated by the vapor permeation film for re-use, a vapor permeation waste water discharged from a bottom of the vapor permeation film and directly transferred to the distillation tower, or indirectly transferred to the distillation tower through the third control valve, wherein the third product is generated through the distillation tower, the extracting distiller, and the vapor permeation film under control of the first control valve, the second control valve, and the third control valve when the first input liquid is fed, wherein the fourth product is generated through the distillation tower and the vapor permeation film under control of the first control valve, the second control valve, and the third control valve when the first input liquid is fed but the second input liquid and the third input liquid are not fed, wherein the fifth product is generated through the extracting distiller and the vapor permeation film under control of the second control valve and the third control valve when the second input liquid is fed but the first input liquid is not fed, wherein the sixth product is generated through the vapor permeation film when the third input liquid is directly fed into the vapor permeation film.

2. The system as claimed in claim 1, wherein the extracting distiller comprising:

a plurality of liquid input pipes provided at a side of the extracting distiller for feeding the first distillation concentrated product, the second input liquid, and the extract agent reflow liquid;

a gas output pipe provided at the top of the extracting distiller for discharging a distillation vapor, a part of the distillation vapor condensing and forming a condensed liquid, the part of the condensed liquid feeding the extracting distiller through a reflow pipe provided at the top of the extracting distiller, part of the condensed liquid discharged and serving as the extract distillation concentrated product;

a liquid output pipe provided at the bottom of the extracting distiller for discharging a part of a liquid left in the extracting distiller as the extract agent recovery liquid, the part of the liquid left in the extracting distiller further heated and evaporating to form an extract agent recovery vapor, the extract agent recovery vapor feeding in the extracting distiller through a gas input pipe configured at the bottom of the extracting distiller;

a plurality of moving plates, each moving plate horizontally provided and having a center through-hole;

a plurality of moving circulating loops provided on the moving plates;

a plurality of static plates, each static plate horizontally provided and having a center through-hole;

a plurality of static circulating loops provided on the static plates;

a plurality of conducting pipes penetrating the static plates and the moving plates;

a rotation axis vertically provided at a center of the extracting distiller; and a case body enveloping the moving plates, the moving circulating loops, the gas input pipe, the liquid input pipes, the static plates, the static circulating loops, the gas output pipe, the conducting pipes, the reflow pipe, the liquid output pipes, and the rotation axis, each of the moving plates provided under the corresponding static plate, the rotation axis inserted through the center through-holes of the moving plates and the static plates, the moving circulating loops and the static circulating loops forming a plurality of circulating channels for the first distillation concentrated product and the second input liquid passing through, each of the conducting pipes configured close to the rotation axis to form a plurality of gas-liquid circulating channels to provide the first distillation concentrated product, the second input liquid, and the extract agent reflow liquid to contact and further pass through.

3. The system as claimed in claim 1, wherein the extract agent recover comprising:

a plurality of liquid input pipes provided at a side of the extract agent recover for feeding the extract agent recovery liquid;

a gas output pipe provided at the top of the extract agent recover for discharging a distillation vapor, the distillation vapor condensing and forming a condensed liquid, a part of the condensed liquid feeding the extract agent recover through a reflow pipe provided at the top of the extract agent recover, the other part of the condensed liquid discharged and serving as the recovery reflow liquid;

a liquid output pipe provided at the bottom of the extract agent recover for discharging a part of a liquid left in the extract agent recover as the extract agent reflow liquid, the part of the liquid left in the extract agent recover further heated and evaporating to form an extract agent reflow vapor, the extract agent reflow vapor feeding in the extract agent recover through a gas input pipe at the bottom of the extract agent recover;

a plurality of moving plates, each moving plate horizontally provided and having a center through-hole;

a plurality of moving circulating loops provided on the moving plates;

a plurality of static plates, each static plate horizontally provided and having a center through-hole;

a plurality of static circulating loops provided on the static plates;

a plurality of conducting pipes penetrating the static plates and the moving plates;

a rotation axis vertically provided at a center of the extract agent recover; and a case body enveloping the moving plates, the moving circulating loops, the gas input pipe, the liquid input pipes, the static plates, the static circulating loops, the gas output pipe, the conducting pipes, the reflow pipe, the liquid output pipes, and the rotation axis, each of the moving plates provided under the corresponding static plate, the rotation axis inserted through the center through-holes of the moving plates and the static plates, the moving circulating loops and the static circulating loops forming a plurality of circulating channels for the extract agent recovery liquid to pass through, each of the conducting pipes configured close to the rotation axis to form a plurality of gas-liquid circulating channels to provide the extract agent recovery liquid to pass through.

4. The system as claimed in claim 1, wherein the third product contains a concentration of isopropanol equal to or more than 99.9% by weight, the fourth product contains a concentration of isopropanol equal to or more than 99.5% by weight, the fifth product contains a concentration of isopropanol equal to or more than 99.5% by weight, and the sixth product contains a concentration of isopropanol equal to or more than 99.5% by weight.

5. The system as claimed in claim 1, wherein the vapor permeation film is provided with a heating evaporator and a vapor permeation film for implementing separation of solvent and water, a dissolver and a diffuser to increase the concentration of isopropanol, the heating evaporator is employed to heat the second distillation concentrated product and the extract distillation liquid to evaporate and form a heated vapor comprising water vapor and isopropanol, the heated vapor flows through a shell side of the vapor permeation film, the water vapor in the heated vapor diffuses and further penetrates the vapor permeation film to arrive at and be discharged from a pipe side of the vapor permeation film through the dissolver and the diffuser, and isopropanol in the heated vapor is left in the shell side.

6. The system as claimed in claim 5, wherein the vapor permeation film comprises at least one of Polyvinyl alcohol (PVA), Polyacrylamide (PAM), Polyacrylonitrile (PAN), Cellulose acetate (CA), 4 (Nylon-4), Polysulfone (PSU), Polyethersulfone (PES), Chitosan, Polyimide (PI), a ceramic film, a metal film, molecular screen film, a carbon film, and an organic-inorganic composite film, and the organic-inorganic composite film employs an inorganic film as a supporting layer, and an organic film stacked on the inorganic film as a selective layer.

7. A system of concentrating and separating waste solvent liquid, comprising:

an ultra gravitational bed for receiving and processing a first input liquid through distillation and condensation to generate a distillation product and a distillation waste water, the distillation waste water discharged through a bottom of the ultra gravitational bed, the distillation product transferred from a top of the ultra gravitational bed, the first input liquid containing a first input concentration of isopropanol, the distillation product containing a distillation concentration of isopropanol higher than the first input concentration, the first input concentration equal to or higher than 5% by weight of the first input liquid, the distillation concentration within 85 to 87.5% by weight of the first input liquid, the distillation product entering a first control valve to split into and transfer a seventh product, a first distillation concentrated product, and a second distillation concentrated product, the seventh product being discharged for re-use;

an extracting distiller an extract agent, the extract agent comprising ethylene glycol, the extracting distiller connected to the first control valve for receiving the first distillation concentrated product and a second input liquid, the second input liquid containing a second input concentration of isopropanol, the second input concentration equal to or higher than 80% by weight of the second input liquid, a mixture of the first distillation concentrated product and the extract agent or a mixture of the extract agent and the second input liquid treated through a process of extraction and distillation to generate an extract agent recovery liquid and an extract distillation concentrated product, the extract agent recovery liquid discharged from a bottom of the extracting distiller, the extract agent recovery liquid comprising a recovery concentration of the extract agent, the extract distillation concentrated product containing an extract distillation concentration of isopropanol higher than the distillation concentration, the extract distillation concentration equal to or higher than 99.5% by weight of the extract agent recovery liquid, the extract distillation concentrated product discharged from a top of the extracting distiller and then transferred to a second control valve, the second control valve splitting the extract distillation concentrated product into a eighth product and an extract distillation liquid, the eighth product being for re-use;

an extract agent recover connected to the extracting distiller and the ultra gravitational bed for receiving the extract agent recovery liquid from the extracting distiller, the extract agent recovery liquid treated by the extract agent recover to generate an extract agent reflow liquid and a recovery reflow liquid, the extract agent reflow liquid discharged from a bottom of the extract agent recover and transferred to the extracting distiller, the recovery reflow liquid discharged from a top of the extract agent recover, the extract agent reflow liquid containing a reflow concentration of the extract agent, the recovery reflow liquid containing a recovery reflow concentration of the extract agent lower than the reflow concentration, the recovery reflow liquid directly transferred to the ultra gravitational bed or indirectly transferred to the ultra gravitational bed through a third control valve; and a vapor permeation film connected to the first control valve and the second control valve for receiving the second distillation concentrated product, the extract distillation liquid, and a third input liquid, at least one of a ninth product, a tenth product, a eleventh product, and a twelfth product being generated by the vapor permeation film for re-use, a vapor permeation waste water discharged from a bottom of the vapor permeation film and directly transferred to the ultra gravitational bed, or indirectly transferred to the ultra gravitational bed through the third control valve, wherein the ninth product is generated through the ultra gravitational bed, the extract distillation unit, and the vapor permeation film under control of the first control valve, the second control valve, and the third control valve when the first input liquid is fed, wherein the tenth product is generated through the ultra gravitational bed and the vapor permeation film under control of the first control valve, the second control valve, and the third control valve when the first input liquid is fed but the second input liquid and the third input liquid are not fed, wherein the eleventh product is generated through the extract distillation unit and the vapor permeation film under control of the second control valve and the third control valve when the second input liquid is fed but the first input liquid is not fed, wherein the twelfth product is generated through the vapor permeation film when the third input liquid is directly fed into the vapor permeation film.

8. The system as claimed in claim 7, wherein the ultra gravitational bed comprising:

a plurality of liquid input pipes provided at a side of the ultra gravitational bed for feeding the first input liquid, the recovery reflow liquid, and the vapor permeation waste water;

a gas output pipe provided at the top of the ultra gravitational bed for discharging a distillation vapor, the distillation vapor condensing and forming a condensed liquid, a part of the condensed liquid feeding in the ultra gravitational bed through a reflow pipe provided at the top of the ultra gravitational bed, the other part of the condensed liquid discharged and serving as the distillation product;

a liquid output pipe provided at the bottom of the ultra gravitational bed for discharging a part of a liquid left in the ultra gravitational bed as the evaporation waste water, the other part of the liquid left in the ultra gravitational bed further heated and evaporating to form an vapor, the vapor feeding the ultra gravitational bed through a gas input pipe provided at the bottom of the ultra gravitational bed;

a plurality of moving plates, each moving plate horizontally provided and having a center through-hole;

a plurality of moving circulating loops provided on the moving plates;

a plurality of static plates, each static plate horizontally provided and having a center through-hole;

a plurality of static circulating loops provided on the static plates;

a plurality of conducting pipes penetrating the static plates and the moving plates;

a rotation axis vertically provided at a center of the ultra gravitational bed; and a case body enveloping the moving plates, the moving circulating loops, the gas input pipe, the liquid input pipes, the static plates, the static circulating loops, the gas output pipe, the conducting pipes, the reflow pipe, the liquid output pipes, and the rotation axis, each of the moving plates provided under the corresponding static plate, the rotation axis inserted through the center through-holes of the moving plates and the static plates, the moving circulating loops and the static circulating loops forming a plurality of circulating channels for gas and liquid to contact and further pass through.

9. The system as claimed in claim 7, wherein the extracting distiller comprising:

a plurality of liquid input pipes provided at a side of the extracting distiller for feeding the first distillation concentrated product, the second input liquid, and the extract agent reflow liquid;

a gas output pipe provided at the top of the extracting distiller for discharging a distillation vapor, the distillation vapor condensing and forming a condensed liquid, a part of the condensed liquid feeding the extracting distiller through a reflow pipe provided at the top of the extracting distiller, the other part of the condensed liquid discharged and serving as the extract distillation concentrated product;

a liquid output pipe provided at the bottom of the extracting distiller for discharging part of a liquid left in the extracting distiller as the extract agent recovery liquid, the extract agent recovery liquid further heated and evaporating to form an extract agent recovery vapor, the extract agent recovery vapor feeding the extracting distiller through a gas input pipe provided at the bottom of the extracting distiller;

a plurality of moving plates, each moving plate horizontally provided and having a center through-hole;

a plurality of moving circulating loops provided on the moving plates;

a plurality of static plates, each static plate horizontally provided and having a center through-hole;

a plurality of static circulating loops provided on the static plates;

a plurality of conducting pipes penetrating the static plates and the moving plates;

a rotation axis vertically provided at a center of the extracting distiller; and a case body enveloping the moving plates, the moving circulating loops, the gas input pipe, the liquid input pipes, the static plates, the static circulating loops, the gas output pipe, the conducting pipes, the reflow pipe, the liquid output pipes, and the rotation axis, each of the moving plates provided under the corresponding static plate, the rotation axis inserted through the center through-holes of the moving plates and the static plates, the moving circulating loops and the static circulating loops forming a plurality of circulating channels for the first distillation concentrated product and the second input liquid to pass through, each of the conducting pipes configured close to the rotation axis to form a plurality of gas-liquid circulating channels to provide for the first distillation concentrated product, the second input liquid, and the extract agent reflow liquid to contact and further pass through.

10. The system as claimed in claim 7, wherein the extract agent recover comprising:

a plurality of liquid input pipes provided at a side of the extract agent recover for feeding the extract agent recovery liquid;

a gas output pipe provided at the top of the extract agent recover for discharging a distillation vapor, the distillation vapor condensing and forming a condensed liquid, a part of the condensed liquid feeding in the extract agent recover through a reflow pipe provided at the top of the extract agent recover, the other part of the condensed liquid discharged and serving as the recovery reflow liquid;

a liquid output pipe provided at the bottom of the extract agent recover for discharging a part of a liquid left in the extract agent recover as the extract agent reflow liquid, the other part of the liquid left in the extract agent recover further heated and evaporating to form an extract agent reflow vapor, the extract agent reflow vapor feeding in the extract agent recover through a gas input pipe at the bottom of the extract agent recover;

a plurality of moving plates, each moving plate horizontally provided and having a center through-hole;

a plurality of moving circulating loops provided on the moving plates;

a plurality of static plates, each static plate horizontally provided and having a center through-hole;

a plurality of static circulating loops provided on the static plates;

a plurality of conducting pipes penetrating the static plates and the moving plates;

a rotation axis vertically provided at a center of the extract agent recover; and a case body enveloping the moving plates, the moving circulating loops, the gas input pipe, the liquid input pipes, the static plates, the static circulating loops, the gas output pipe, the conducting pipes, the reflow pipe, the reflow pipe, the liquid output pipes, and the rotation axis, each of the moving plates provided under the corresponding static plate, the rotation axis inserted through the center through-holes of the moving plates and the static plates, the moving circulating loops and the static circulating loops forming a plurality of circulating channels for the extract agent recovery liquid to pass through, each of the conducting pipes provided close to the rotation axis to form a plurality of gas-liquid circulating channels provided for the extract agent recovery liquid to pass through.

11. The system as claimed in claim 7, wherein the vapor permeation film is provided with a heating evaporator and a vapor permeation film for implementing separation of solvent and water, a dissolver and a diffuser to increase the concentration of isopropanol, the heating evaporator is employed to heat the second distillation concentrated product and the extract distillation liquid to evaporate and form a heated vapor comprising water vapor and isopropanol, the heated vapor flows through a shell side of the vapor permeation film, the water vapor in the heated vapor diffuses and further penetrates the vapor permeation film to arrive at and be discharged from a pipe side of the vapor permeation film through the dissolver and the diffuser, and isopropanol in the heated vapor is left in the shell side.

12. The system as claimed in claim 11, wherein the vapor permeation film comprises at least one of Polyvinyl alcohol (PVA), Polyacrylamide (PAM), Polyacrylonitrile (PAN), Cellulose acetate (CA), 4 (Nylon-4), Polysulfone (PSU), Polyethersulfone (PES), Chitosan, Polyimide (PI), a ceramic film, a metal film, molecular screen film, a carbon film, and an organic-inorganic composite film, and the organic-inorganic composite film employs an inorganic film as a supporting layer, and an organic film stacked on the inorganic film as a selective layer.

13. The system as claimed in claim 7, wherein the ninth product contains a concentration of isopropanol equal to or more than 99.9% by weight, the tenth product contains a concentration of isopropanol equal to or more than 99.5% by weight, the eleventh product contains a concentration of isopropanol equal to or more than 99.5% by weight, and the twelfth product contains a concentration of isopropanol equal to or more than 99.5% by weight.

* * * * *